US010126236B2

(12) United States Patent
Battefeld et al.

(10) Patent No.: US 10,126,236 B2
(45) Date of Patent: Nov. 13, 2018

(54) METHOD FOR DETECTION OF THE CONTAMINATION OF A SAMPLE CUVETTE OF A NEPHELOMETRIC TURBIDIMETER

(71) Applicant: HACH LANGE GMBH, Berlin (DE)

(72) Inventors: Manfred Battefeld, Duesseldorf (DE); Michael Kussmann, Duesseldorf (DE); Bas De Heij, Dormagen (DE); Bernd Gassner, Neuss (DE); Frank Steinhauer, Berlin (DE); Hans-Joachim Kumpch, Berlin (DE); Axel Leyer, Moenchengladbach (DE); Michael Kueppers, Kaarst (DE); Andreas Golitz, Moers (DE); Andreas Mitreiter, Kleinmachnow (DE); Clemens Hanschke, Berlin (DE); Lothar Heidemanns, Korschenbroich (DE)

(73) Assignee: HACH LANGE GMBH, Berlin (DE)

( * ) Notice: Subject to any disclaimer, the term of this patent is extended or adjusted under 35 U.S.C. 154(b) by 0 days.

(21) Appl. No.: 15/806,343

(22) Filed: Nov. 8, 2017

(65) Prior Publication Data
US 2018/0059016 A1 Mar. 1, 2018

Related U.S. Application Data

(62) Division of application No. 15/025,553, filed as application No. PCT/EP2013/070353 on Sep. 30, 2013, now Pat. No. 9,851,297.

(51) Int. Cl.
*G01N 21/00* (2006.01)
*G01N 21/15* (2006.01)
(Continued)

(52) U.S. Cl.
CPC ......... *G01N 21/47* (2013.01); *G01N 21/4785* (2013.01); *G01N 21/51* (2013.01);
(Continued)

(58) Field of Classification Search
None
See application file for complete search history.

(56) References Cited

U.S. PATENT DOCUMENTS 3,497,690 A * 2/1970 Bahr .................. G01N 15/12
250/369
3,727,066 A * 4/1973 Louderback ....... G01N 21/8507
250/214 B
(Continued)

FOREIGN PATENT DOCUMENTS

| CN | 2068681 | 1/1991 |
|----|---------|--------|
| CN | 101532946 | 9/2009 |

(Continued)

OTHER PUBLICATIONS

CN Office Action, State Intellectual Property Office of the People's Republic of China, dated Jan. 10, 2018, pp. 8.
(Continued)

*Primary Examiner* — Dominic J Bologna
*Assistant Examiner* — Jarreas C Underwood
(74) *Attorney, Agent, or Firm* — Norman B. Thot

(57) ABSTRACT

A method for detecting a contamination of a cuvette of a turbidimeter. The turbidimeter includes a light source which emits a light beam directed to a cuvette, a scattering light detector, and a diffuser with a body and an actuator. The actuator moves the body between a parking position and a test position where the body is between the measurement light source and the cuvette, thereby interferes with the light beam, and generates a diffuse test light entering the cuvette. The method includes activating the actuator to move the
(Continued)

body from the parking position into the test position, activating the light source, measuring a test light intensity received by the scattering light detector, comparing the test light intensity with a reference light intensity, and generating a contamination signal if a difference between a reference light intensity and the test light intensity measured exceeds a first threshold value.

4 Claims, 3 Drawing Sheets

(51) Int. Cl.
  *G01N 21/47* (2006.01)
  *G01N 21/51* (2006.01)
  *G01N 21/94* (2006.01)
(52) U.S. Cl.
  CPC .......... *G01N 21/15* (2013.01); *G01N 21/94* (2013.01); *G01N 2021/152* (2013.01); *G01N 2021/157* (2013.01); *G01N 2021/473* (2013.01); *G01N 2021/4726* (2013.01); *G01N 2201/0634* (2013.01)

(56) References Cited

U.S. PATENT DOCUMENTS

| | | | | | |
|---|---|---|---|---|---|
| 3,851,976 | A | * | 12/1974 | Meier | G01J 1/1626 250/575 |
| 4,055,768 | A | * | 10/1977 | Bromberg | G01N 21/645 250/461.2 |
| 4,118,625 | A | * | 10/1978 | Underwood | G01N 21/51 250/343 |
| 4,165,179 | A | * | 8/1979 | Sato | G01N 21/15 356/246 |
| 4,305,659 | A | * | 12/1981 | Bilstad | G01N 21/3151 356/40 |
| 4,325,910 | A | * | 4/1982 | Jordan | G01N 21/253 250/564 |
| 5,506,679 | A | * | 4/1996 | Cooper | G01N 21/53 356/338 |
| 5,912,737 | A | * | 6/1999 | Bannerjee | G01N 21/4785 356/243.2 |
| 6,096,272 | A | * | 8/2000 | Clark | G01N 21/253 422/64 |
| 6,307,630 | B1 | * | 10/2001 | Banerjee | G01N 21/253 356/339 |
| 7,663,751 | B1 | * | 2/2010 | Mitchell | G01N 21/51 356/339 |
| 8,345,248 | B2 | * | 1/2013 | Hong | G01N 21/534 356/436 |
| 8,873,052 | B2 | * | 10/2014 | Stengel | G01N 21/274 356/341 |
| 9,182,344 | B1 | * | 11/2015 | Mitchell | G01N 21/534 |
| 9,329,195 | B2 | * | 5/2016 | Oguro | B08B 9/28 |
| 2009/0149776 | A1 | * | 6/2009 | Adams | A61B 5/0059 600/584 |
| 2011/0043807 | A1 | | 2/2011 | Andelic et al. | |
| 2013/0057859 | A1 | | 3/2013 | Stengel et al. | |

FOREIGN PATENT DOCUMENTS

| | | |
|---|---|---|
| CN | 102762972 | 10/2012 |
| CN | 202693474 | 1/2013 |
| CN | 202886281 | 4/2013 |
| GB | 2 010 479 A | 6/1979 |
| JP | 7-243964 A | 9/1995 |
| JP | 2006/153738 A | 6/2006 |

OTHER PUBLICATIONS

English Translation of CN Office Action, State Intellectual Property Office of the People's Republic of China, dated Jan. 10, 2018, pp. 10.

* cited by examiner

METHOD FOR DETECTION OF THE CONTAMINATION OF A SAMPLE CUVETTE OF A NEPHELOMETRIC TURBIDIMETER

CROSS REFERENCE TO PRIOR APPLICATIONS

This application is a divisional of U.S. application Ser. No. 15/025,553, filed on Mar. 29, 2016. U.S. application Ser. No. 15/025,553 is a U.S. National Phase application under 35 U.S.C. § 371 of International Application No. PCT/EP2013/070353, filed on Sep. 30, 2013. The International Application was published in English on Apr. 2, 2015 as WO 2015/043675 A1 under PCT Article 21(2).

FIELD

The present invention relates to a method for detecting a contamination of a sample cuvette of a nephelometric turbidimeter after a contamination test is requested.

BACKGROUND

A nephelometric turbidimeter determines the concentration of solid particles suspended in a liquid sample within a sample cuvette by projecting a light beam into the liquid sample within the cuvette. A light detector detects the amount of light scattered by the suspended solid particles at an angle of at least 30° to the light beam axis, for example, at a right angle to the light beam axis. Not only particles suspended in the liquid sample generate scattered light, however, any optical contamination of the cuvette, such as a fouling layer on the inside of the transparent cuvette wall or scratches at the cuvette body, may also scatter light.

US 2011/0043807 A1 describes a turbidimeter with two separate light sources and two separate light detectors so that different turbidity measurements under different scattering angles and with different penetration distances can be provided. The results of the different turbidity measurements are checked for plausibility, and a warning signal is generated if the different turbidity measurements do not seem plausible. The technical effort is relatively high and strong inhomogeneities of turbidity within the liquid sample can also cause non-plausible measurement results.

SUMMARY

An aspect of the present invention is to provide a simple device for an optical turbidimeter and a simple method for detecting contamination of the liquid sample cuvette.

In an embodiment, the present invention provides a method for detecting a contamination of a sample cuvette of a nephelometric turbidimeter after a contamination test is requested. The nephelometric turbidimeter comprises a measurement light source configured to emit an axial parallel light beam directed to a sample cuvette, a scattering light detector arranged to receive a scattered light from the sample cuvette, and a diffuser comprising a diffuser body and a diffuser actuator. The diffuser actuator is configured to move the diffuser body between a parking position in which the diffuser body does not interfere with the axial parallel light beam, and a test position where the diffuser body is arranged between the measurement light source and the sample cuvette so that the diffuser body interferes with the axial parallel light beam and generates a diffuse test light entering the sample cuvette. The method comprises activating the diffuser actuator to move the diffuser body from the parking position into the test position, activating the measurement light source, measuring a test light intensity received by the scattering light detector, comparing the test light intensity measured with a reference light intensity, and generating a contamination signal if a difference between a reference light intensity and the test light intensity measured exceeds a first threshold value.

BRIEF DESCRIPTION OF THE DRAWINGS

The present invention is described in greater detail below on the basis of embodiments and of the drawings in which.

DETAILED DESCRIPTION

Figure 1:
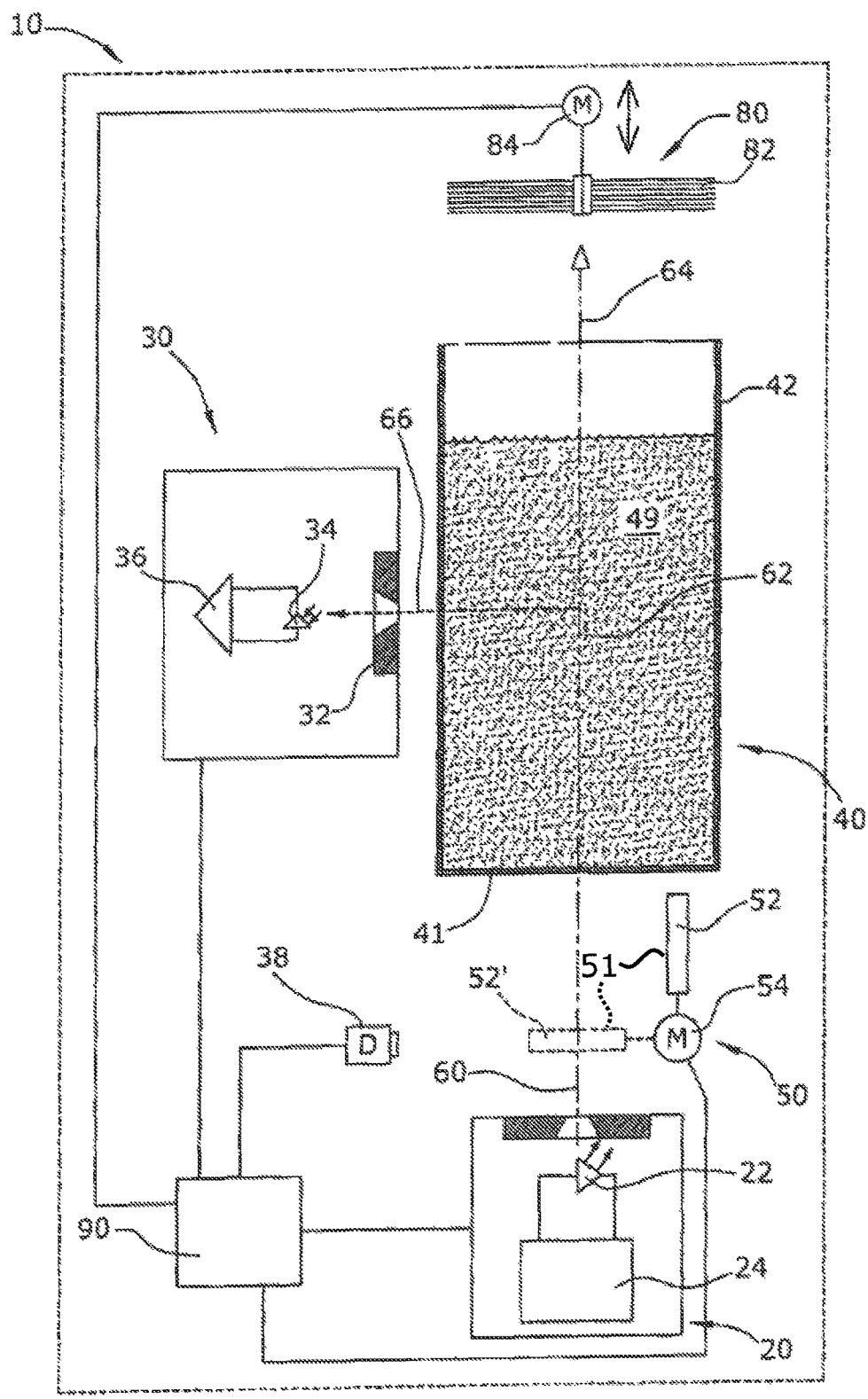
FIG. 1 shows a turbidimeter with a switchable diffuser in a parking position.

The nephelometric turbidimeter for measuring turbidity in a liquid sample according to the present invention is provided with a transparent sample cuvette which can be completely transparent, or which can be at least in part transparent to define two or more optical windows. The turbidimeter can be provided as a laboratory device for using exchangeable cuvettes which are already filled with the liquid sample when inserted into the turbidimeter, or can be provided as a process device for quasi-continuous measurement with a static cuvette with a liquid sample inlet and a liquid sample outlet for continuously transporting the liquid sample into the cuvette. The present invention is particularly advantageous for a process device where the cuvette is used for a long period of time without being exchanged and where fouling on the inside of the cuvette body is a problem.

The turbidimeter is provided with a measurement light source for emitting an axial parallel light beam directed into the cuvette. The axial direction is defined by the light beam itself, not by the cuvette. The light beam can, for example, be generated by a light emitting diode (LED), such as by a laser LED. The diameter of the light beam is normally between 0.5 mm and a few millimeters. The monochromatic light beam generated by a laser LED has high optical qualities, but is very sensitive to cuvette contamination. A plausible and reliable detection of cuvette contamination is therefore particularly important for a turbidimeter with a laser LED as a light source.

The turbidimeter is provided with a scattering light detector arranged to receive scattered light emerging from the cuvette containing the liquid sample. The scattering light detector is not arranged axially in-line with the light beam so that the scattering light detector does not receive light coming directly from the measurement light source and in this regards is nephelometric in design. The scattering light detector only receives light source light which is reflected by particles of the liquid sample into a non-axial direction.

The scattering light detector can, for example, be arranged in a more or less right angle with respect to the axial light beam. In an embodiment, the scattering light detector can, for example, receive at least a very small sector of a few degrees or of even less than 1°, or alternatively can be realized as a circumferential detector arrangement which receives and collects the scattered light over the complete circumference of 360° with respect to the light beam axis.

The turbidimeter is provided with a switchable diffuser with an optical diffuser body and with a diffuser actuator for moving the diffuser body between a first, or parking position, and a second, or test position. In the parking position, the diffuser body does not interfere with the emitted light beam so that the light beam enters the cuvette as a concentrated parallel light beam. In the test position, the diffuser body has been moved into a position between the light source and the cuvette in which the diffuser body interferes with the emitted light beam to generate diffuse test light entering the cuvette. If the diffuser is switched into the test position, the parallel light beam coming from the measurement light source is changed into a diffuse light generator located in the diffuser body. The cuvette containing the liquid sample is consequently exposed to diffuse light only in the test mode. In an alternative embodiment, the diffuse light generator can be a separate switchable diffuse light source independent and separate of the measurement light source.

A contamination test can be executed at any time with the turbidimeter comprising the switchable diffuser by using the scattering light detector to determine the scattered test light caused by the light of the diffuse light generator which is reflected by particles adhering to the cuvette body or by scratches etc. at the cuvette body. The contamination test can, for example, be requested and executed after every turbidity measurement of a liquid sample to control the plausibility of the measurement value of the turbidity measurement with help of the contamination test measurement value. Alternatively or additionally, the contamination test can be executed in periodic intervals, for example, every couple of hours or every day, with or without a liquid test solution. The contamination test generally can be practiced with an empty cuvette, with the cuvette filled with a clear reference liquid, or filled with the sample liquid. The contamination test as well as the reference measurement can, for example, be done with a clear test solution in the cuvette.

The method for detecting contamination of a sample cuvette of the turbidimeter occurs pursuant to the following method steps after a contamination test has been requested:
  activating the diffuser actuator to move the diffuser body from its parking position into its test position,
  activating the light source,
  measuring the test light intensity (It) received by the scattering light detector,
  comparing the measured test light intensity (It) with a reference scattering light intensity (Ir), and
  generating a contamination signal if the difference between the reference light intensity (Ir) and the measured test light intensity (It) exceeds a threshold value.

The reference light intensity (Ir) can be a reference value memorized in a look-up table of a reference memory in which an expected reference light intensity (Ir) is memorized for every sample measurement intensity (I). If the measured test light intensity (It) is more or less equal to the memorized reference light intensity (Ir) for this particular sample measurement intensity (I), then the plausibility is good, and no contamination signal is generated. This procedure allows for a determination of the plausibility of every sample measurement to be controlled.

In addition or alternatively, the reference light intensity (Ir) can be a single calibration value which is based on a reference measurement made with a clean cuvette and a clean reference liquid filling the cuvette. The reference light intensity (Ir) can be measured at the end of the turbidimeter production process or can be measured by the user, for example, when a new cuvette is used. The measurement reference light intensity (Ir) is memorized in a reference memory of the turbidimeter. The contamination test can be provided, for example, every morning after the turbidimeter has been started.

A contamination of the cuvette includes every kind of change of the optical transmission characteristics of the cuvette which results in a change of the originally non-diffuse optical characteristics of the cuvette. In particular, scratches, tarnishing, dirt, fingerprints, condensate and/or fouling at the inner and/or outer surface of the cuvette can be an optical contamination of the cuvette which can corrupt every sample measurement value.

In an embodiment of the present invention, the cuvette is cylindrical and is provided with a cylinder side wall and a plane bottom wall. The cylindrical side wall allows the scattering light detector to be positioned at every sector angle with respect to the cuvette so that the rotational position of the cuvette within the turbidimeter is not relevant. The cylindrical wall also allows the use of a circumferential scattering light detector arrangement which receives the scattered light from the cuvette not only within a small circumferential sector, but over a large part of or the complete circumference. Axicons are known optical means for collecting scattered light around the circumference of a cuvette.

The plane bottom wall allows for the directing the parallel light beam in a right angle to the bottom wall even if the light beam is not in perfect axial alignment with the longitudinal axis of the cylindrical cuvette. The cylindrical cuvette, including the plane bottom wall, makes the turbidimeter more tolerant with respect to small geometric aberrations between the measurement light source and the cuvette.

In an embodiment of the present invention, a cleaning device is provided for mechanically cleaning the inside of the cuvette cylinder wall. The cleaning device can be a cleaning brush rotated by a cleaning motor. The cleaning brush can also be provided with a shifting arrangement which provides for a vertical movement of the brush into the cuvette to automatically clean the inside of the cuvette cylinder wall on demand. In an embodiment of the present invention, the cleaning means can, for example, be activated if a contamination signal has been generated. When the cleaning device has finished the cleaning action, another contamination test can be requested to verify that the cuvette is no longer contaminated.

In an embodiment of the present invention, a separate light source detector can, for example, be provided which is optically assigned to the diffuser body to directly receive diffuse light from the diffuser body in its test position. The light source detector basically only receives diffuse light coming from the diffuser body in its test position. In a method of the present invention, the measured light source intensity (Ims) is determined by the light source detector and is compared with a memorized reference light source intensity (Irs). A light source failure signal is generated if the difference between the measured and the memorized light source intensity exceeds a threshold value. This provides that the test light intensity (It) is measured with the same light intensity of the light source as the reference light intensity (Ir).

In an embodiment of the present invention, the scattering body can, for example, be made of a transparent matrix material filled with scattering particles. The matrix material can, for example, be a transparent plastic substance homogeneously filled with scattering particles which can be micro-particles. The plastic substance can be PMMA or another highly transparent substance. The particles can, for example, be calcium phosphate, fluorides, stannic oxide, titanium oxide, or other suitable particle powders. The particle size should be in the range of the wavelength of the light generated by the light source and/or in the range of the sensibility wavelength of the light detector, for example, in the range of 1.0 to 5.0 µm.

The scattering body can alternatively be made of frosted glass or a similar scattering body which is basically completely transparent but is somehow frosted at one or both of its surfaces.

In an embodiment of the present invention, the measurement light source can, for example, be arranged axially with respect to the cuvette and below the plane bottom wall of the cuvette. This arrangement allows a cuvette holding arrangement which is easily accessible from the top so that the cuvette can simply be introduced, or removed vertically, from or to the top, respectively.

The present invention is described in greater detail below on the basis of an embodiment and of the drawings.

The drawings show a turbidimeter 10 for measuring and detecting the turbidity of a liquid sample 49 in a sample cuvette 40. In the present embodiment, the turbidimeter 10 is a so-called process device, and not a so-called laboratory device. The turbidimeter 10 is therefore provided with a sample inlet and with a sample outlet arrangement which is not shown in the drawings and which continuously or non-continuously pumps liquid samples into the sample cuvette 40. The cuvette 40 is not exchanged for a relatively long period of time, for example, for a couple of days or even for months.

The turbidity of a liquid is an indication of the concentration of solid particles suspended in the liquid sample 49. The turbidity is determined by projecting a light beam 64 into the liquid sample 49 and by measuring the light intensity of the light scattered by the liquid sample 49 at an angle of 90° with respect to the light beam's longitudinal axis within the liquid sample 49.

The turbidimeter 10 is provided with a housing with an opening at the top for inserting and ejecting the sample cuvette 40 into and from a suitable cuvette receiving device inside the housing (not shown in the drawings). The cuvette receiving device positions the inserted sample cuvette 40 in a defined cuvette position. The sample cuvette 40 is cylindrical in shape and is provided with a vertical cylinder wall 42 and a horizontal plane bottom wall 41, which together both define the cuvette body. The cuvette body is made out of transparent and colorless glass.

A measurement light source 20 is arranged under the cuvette's horizontal plane bottom wall 41. The measurement light source 20 is provided with an electric LED driver 24 to electrically drive a light emitting diode (LED) 22 which is provided as a laser LED. The measurement light source 20 emits an axial parallel laser light beam 60 directed to the sample cuvette 40. The light beam 60 emitted crosses the horizontal plane bottom wall 41 at a right angle and passes through the liquid sample 49 within the cuvette body as a measurement beam 62, as shown in FIG. 1.

A scattering light detector 30 is arranged radially adjacent to the sample cuvette 14 to receive scattered light 66 scattered in a right angle with respect to the axis of the measurement beam 62. The scattering light detector 30 is provided with an aperture 32, with a photodiode 34, and with an operational amplifier 36 for amplifying the signal of the photodiode 34.

Figure 2:
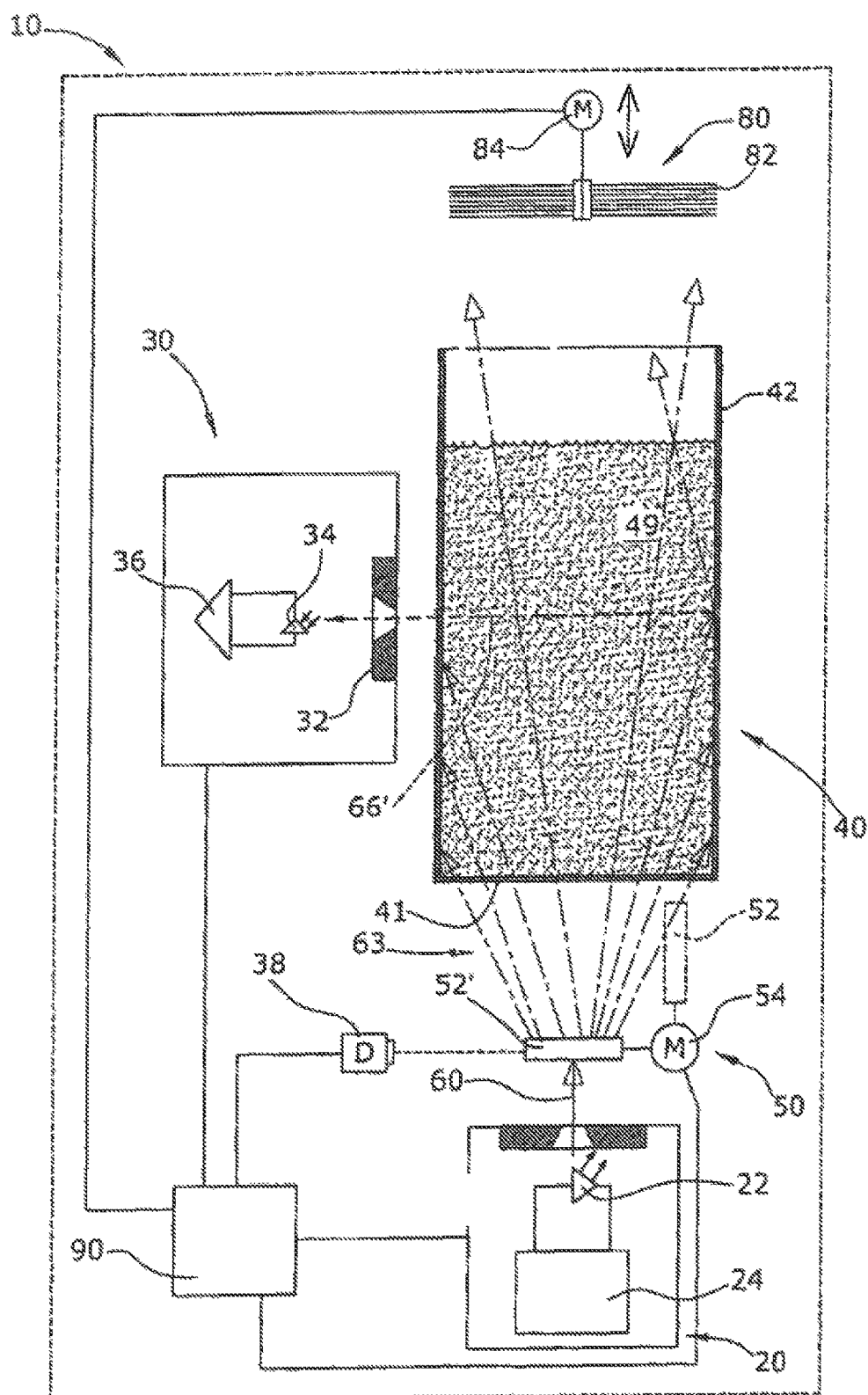
FIG. 2 shows the turbidimeter of FIG. 1 with the switchable diffuser in a test position and with a clean cuvette.
Figure 3:
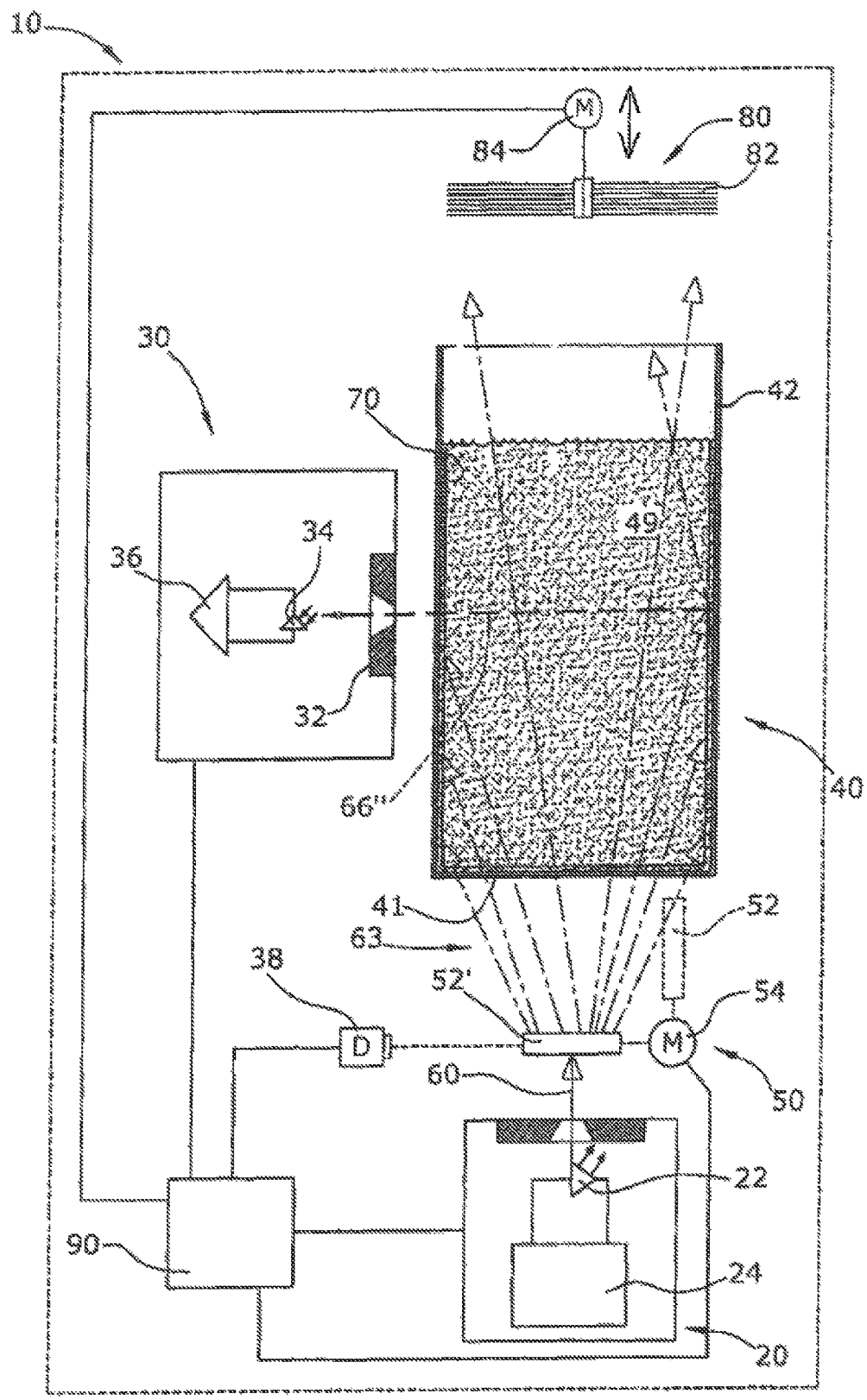
FIG. 3 shows the turbidimeter of FIG. 2 with a contaminated cuvette.

A switchable diffuser 50 with an optical diffuser body 51 in a first position 52 and a diffuser actuator 54 are arranged axially and vertically between the measurement light source 20 and the sample cuvette 40. The diffuser body 51 can be moved by the diffuser actuator 54 between a parking position 52, shown in FIG. 1, and a test position 52' shown in FIGS. 2 and 3. The diffuser body 51 does not interfere with the light beam 60 emitted in the parking position 52. In the test position 52', as shown in FIGS. 2 and 3, the diffuser body 51 interferes with the light beam 60 emitted to generate diffuse test light 63 entering the sample cuvette 40. The diffuser body 51, consists of a transparent matrix material filled with solid opaque scattering particles. The diffuser actuator 54 is a simple and reliable electric actuator which pivots the diffuser body 51, into the test position 52' when the diffuser actuator 54 is electrically activated.

A cleaning device 80 is provided above the cuvette 40 for mechanically cleaning the inside of the vertical cylinder wall 42 and of the horizontal plane bottom wall 41. The cleaning device 80 is provided with a cleaning brush 82 which is rotated by an electric cleaning motor 84. The cleaning device 80 is also provided with a shifting device for verticality moving the cleaning brush 82 through the sample cuvette's 14 top opening into the sample cuvette 40 to thereby allow the cleaning brush 82 to clean the inner surfaces of the sample cuvette 40.

A separate light source detector 38 is arranged close to the diffuser body 51 in its test position 52' to directly receive diffuse test light coming from the diffuser body 51 in its test position 52'. The light source detector 38 can be a photodiode.

The turbidimeter 10 is provided with a control device 90 for controlling all electric elements of the turbidimeter 10. The control device 90 is electrically connected to the measurement light source 20, the diffuser 50, the scattering light detector 30, the light source detector 38, and the cleaning device 80.

FIG. 1 shows the measurement mode of the turbidimeter 10 so that the diffuser 50 is in its parking position 52. The measurement light source 20 is activated in the measurement mode so that an light beam 60 is generated which passes through the liquid sample 49 as a parallel measurement beam 62. In a turbid liquid sample 49, the measurement beam 62 causes scattered light in all directions, of which only the radially scattered light 66 in the radial plane of the scattering light detector 30 is received by the scattering light detector 30. The sample measurement light intensity (I) detected by the scattering light detector 30 is converted by the control device 90 into a liquid turbidity value according to well-understood principles.

If the control device 90 initiates a contamination test, the control device 90 causes the diffuser actuator 54 to pivot the diffuser body 51 into its test position 52' as shown in FIGS. 2 and 3. A contamination test can be initiated on a periodic basis and/or can be initiated manually and/or can be initiated by other incidences, such as extreme liquid turbidity values etc.

The diffuser body 51 in its test position 52' causes the light beam 60 to become diffuse so that the diffuser body 51 is a diffuse light generator directing diffuse test light 63 to the sample cuvette 40 which passes through the liquid sample 49. The diffuse test light 63, as shown in FIGS. 2 and 3, causes a different scattering light intensity of the radially scattered test light 66',66" received by the scattering light detector 30, compared to the scattered sample measurement light 66 caused by a concentrated parallel measurement beam 62, as shown in FIG. 1. The intensity of the radially scattered test light 66', 66" also depends on the contamination of the sample cuvette 40, and in particular on the contamination of the inner surface of the vertical cylinder wall 42. FIG. 3 shows the sample cuvette 40 with a contamination layer 70 on the inner surface of the vertical cylinder wall 42. The contamination layer 70 can, for example, be fouling which can accumulate after a while at the inner surface of the sample cuvette 14. The contamination layer 70 diffuses light so that the radially scattered test light 66'' received by the scattering light detector 30 has a different intensity compared to that without a contamination layer 70.

At the end of a turbidimeter manufacturing process, a reference light intensity (Ir) is determined with the diffuser 50 in the test position 52', as shown in FIG. 2. The reference light intensity (Ir) is memorized in a digital memory of the digital control device 90. A contamination test is periodically triggered during the operational life of the turbidimeter 10. When the contamination test has been triggered or is manually requested, the control device 90 causes the diffuser 50 to change into the test mode so that the measurement light source 20 is activated, and the activated diffuser actuator 54 pivots the diffuser body 51 into its test position 52' as shown in FIGS. 2 and 3. The scattering light detector 30 receives the radially scattered test light 66', 66'' and the control device 90 determines a test light intensity (It) from the signal received by the scattering light detector 30. The control device 90 compares the measured test light intensity (It) with the memorized reference light intensity (Ir) and generates a contamination signal if the difference between the intensities exceeds a threshold value.

If a contamination signal has been generated, a contamination layer 70 at the inner side of the vertical cylinder wall 42 is the most probable cause therefor. The control device 90 can therefore be programmed to cause a cleaning action so that the cleaning device 80 is activated to clean the inner surface of the cuvette body of the sample cuvette 40. After the cleaning device 80 has finished the cleaning action, the control device 90 requests another contamination test to determine if the contamination layer 70 has been successfully removed from the inner side of the sample cuvette 40.

The diffuser 50 can also be used to control the intensity and the beam quality of the light beam 60 emitted by the measurement light source 20. In the test position 52' of the diffuser 50, the diffuser body 51 irradiates diffuse test light 63 into all spatial directions of which a small fraction is received by the light source detector 38.

A reference light source intensity (Irs) is measured and memorized in the control unit 90 at the end of a turbidimeter manufacturing process. When the turbidimeter 10 is in the test mode and the diffuser body 51 is in its test position 52', the measured light source intensity (Ims) measured by the light source detector 38 is compared with the memorized reference light source intensity (Irs) by the control unit 90. A light source warning signal is generated if the difference between the light source intensities (Irs) and (Ims) exceeds a memorized threshold value.

Alternatively or additionally, the difference of the light source intensity (Ims) and the reference light source intensity (Irs) is used as a basis to normalize the light energy of the light beam 60 emitted by the measurement light source 20 to the level defined by the reference light source intensity (Irs). The electric energy (Em) which is necessary to generate the reference measuring light intensity is compared to a reference value (Er), and a lifetime signal is generated if the difference between the needed electric energy (Em) and the reference value (Er) exceeds a threshold value (dE). If the measurement light source 20 needs more and more electric energy to generate measuring light with the reference light source intensity (Irs), then the reason generally is the decreasing electric efficiency of the measurement light source 20 which is an indication for an end of the light source lifetime.

The present invention is not limited to embodiments described herein; reference should be had to the appended claims.

What is claimed is:

1. A method for detecting a contamination of a sample cuvette of a nephelometric turbidimeter after a contamination test is requested,
the nephelometric turbidimeter comprising:
a measurement light source configured to emit an axial parallel light beam directed to a sample cuvette, the sample cuvette being cylindrical and comprising a cylinder wall;
a scattering light detector arranged to receive a scattered light from the sample cuvette;
a diffuser comprising a diffuser body and a diffuser actuator, the diffuser actuator being configured to move the diffuser body between a parking position in which the diffuser body does not interfere with the axial parallel light beam and a test position where the diffuser body is arranged between the measurement light source and the sample cuvette so that the diffuser body interferes with the axial parallel light beam and generates a diffuse test light entering the sample cuvette; and
a cleaning device configured to perform a mechanical cleaning of an inner side of the cylinder wall,
the method comprising:
activating the diffuser actuator to move the diffuser body from the parking position into the test position;
activating the measurement light source;
measuring a test light intensity received by the scattering light detector;
comparing the test light intensity measured with a reference light intensity;
generating a contamination signal if a difference between a reference light intensity and the test light intensity measured exceeds a first threshold value,
activating the cleaning device if a contamination signal has been generated; and
requesting the contamination test when the cleaning device has finished the mechanical cleaning.

2. The method as recited in claim 1, wherein,
the nephelometric turbidimeter further comprises a light source detector assigned to the diffuser body, the light source detector being configured to directly receive the diffuse test light from the diffuser body when the diffuser body is in the test position, and
when the diffuser body is in the test position, the method further comprises:
measuring a light source intensity received by the light source detector; and
comparing the light source intensity measured with a reference light source intensity.

3. The method as recited in claim 2, wherein the method further comprises:
controlling the intensity of the measurement light source via the light source detector so that the light source intensity is equal to the reference light source intensity.

4. The method as recited in claim 3, wherein the method further comprises:
comparing an electric energy used to generate the reference light source intensity with an electric energy reference, and generating a lifetime signal if a difference exceeds a second threshold value.

* * * * *